(12) United States Patent
Blair

(10) Patent No.: US 6,352,722 B1
(45) Date of Patent: Mar. 5, 2002

(54) DERIVATIZED CARBOHYDRATES, COMPOSITIONS COMPRISED THEREOF AND METHODS OF USE THEREOF

(75) Inventor: Julian A. Blair, St. Ives (GB)

(73) Assignee: Quadrant Holdings Cambridge Limited, Nottingham (GB)

( * ) Notice: Subject to any disclaimer, the term of this patent is extended or adjusted under 35 U.S.C. 154(b) by 0 days.

(21) Appl. No.: 09/218,845

(22) Filed: Dec. 22, 1998

Related U.S. Application Data

(60) Provisional application No. 60/068,754, filed on Dec. 23, 1997.

(51) Int. Cl.[7] .............................. A61K 9/14; A61K 9/20; A61K 31/56
(52) U.S. Cl. ....................... 424/484; 424/464; 424/469; 424/488; 514/178
(58) Field of Search ................................. 424/484, 488, 424/489, 490, 493, 464, 499, 461, 469, 425, 436; 536/123.13; 514/53, 953, 965, 178

(56) References Cited

U.S. PATENT DOCUMENTS

| | | | |
|---|---|---|---|
| 3,948,263 A | 4/1976 | Drake, Jr. et al. | 128/260 |
| 4,244,949 A | 1/1981 | Gupta | 424/243 |
| 4,326,524 A | 4/1982 | Drake, Jr. et al. | 128/260 |
| 4,684,719 A | 8/1987 | Nishikawa et al. | |
| 4,906,463 A | 3/1990 | Cleary et al. | 424/78 |
| 5,006,343 A | 4/1991 | Benson et al. | 424/450 |
| 5,011,678 A | 4/1991 | Wang et al. | 424/45 |
| 5,098,893 A | 3/1992 | Franks et al. | |
| 5,239,993 A | 8/1993 | Evans | 128/203.15 |
| 5,554,388 A | * 9/1996 | Illum | 424/501 |
| 5,608,647 A | 3/1997 | Rubsamen et al. | 364/509 |

FOREIGN PATENT DOCUMENTS

| | | |
|---|---|---|
| EP | 0 356 154 A2 | 2/1990 |
| EP | 0 714 905 A2 | 6/1996 |
| WO | PCT/GB90/00497 | 10/1990 |
| WO | WO 93/09832 | 5/1993 |
| WO | WO 93/10758 | 6/1993 |
| WO | WO 94/08552 | 4/1994 |
| WO | WO 94/13271 | 6/1994 |
| WO | 95/21180 | 8/1995 |
| WO | 96/01832 | 1/1996 |
| WO | PCT/GB95/01861 | 2/1996 |
| WO | 96/03978 | 2/1996 |
| WO | PCT/GB96/01367 | 12/1996 |
| WO | 96/40077 | 12/1996 |
| WO | 99/01463 | 1/1999 |

OTHER PUBLICATIONS

International Search Report on International application No. PCT/GB98/03888, Jul. 1999.

Yasuda (1997) "Method for producing alkyl rutinosides by enzymatic transglyconsidation of rutin" Chemical Abstracts 126 Abstract No. 31577t.

Klein et al. (1987) "High–velocity microprojectiles for delivering nucleic acids into living cells" *Nature* 327:70–73.

Akoh et al. (1987) "One–Stage Synthesis of Raffinose Fatty Acid Polyesters" *Journal of Food Science* 52:1570–1576.

Khan et al. (1993) "Enzymic Regioselective Hydrolysis of Peracetylated Reducing Disaccharides, Specifically at the Anomeric Centre: Intermediates for the Synthesis of Oligosaccharides" *Tetrahedron Letters* 34:7767–7770.

Khan (1984) "Chemistry and New Uses of Sucrose: How Important?" *Pure& Appl Chem.* 56:833–844.

Khan et al. (1990) "Cyclic Acetals of 4,1',6'–Trichloro–4, 1',6'–Trideoxy–galacto–Sucrose and Their Conversion into Methyl Ether Derivatives" *Carbohydrate Research* 198:275–283.

Lindberg (1993) "Creating the Future for Portable Inhalers" Summary of Lecture at Management Forum Dec. 6–7, 1993.

\* cited by examiner

*Primary Examiner*—Michael G. Hartley
(74) *Attorney, Agent, or Firm*—Morrison & Foerster LLP

(57) ABSTRACT

Derivatized carbohydrates are provided which can be used to form a variety of materials including solid delivery systems. The derivatized carbohydrates are generally carbohydrates, wherein at least a portion of the hydroxyl groups on the carbohydrate are substituted with a branched hydrophobic chain, such as a hydrocarbon chain, via, for example, an ether or ester linkage. The solid delivery systems can be used for delivery and release of a variety of substances, and are, for example, in the form of tablets for oral administration, or in the form of powders, microspheres or implants for intravenous, intradermal, transdermal, pulmonary or other route of administration. The derivatized carbohydrates can be processed to form a solid matrix having a substance, such as a therapeutic agent, incorporated therein. In one embodiment, the solid matrix is provided in a solid dose form which is capable of releasing a therapeutic substance in situ at various controlled rates.

6 Claims, 3 Drawing Sheets ded by molding,
or other techniques.

DERIVATIZED CARBOHYDRATES, COMPOSITIONS COMPRISED THEREOF AND METHODS OF USE THEREOF

CROSS REFERENCE TO RELATED APPLICATIONS

This application claims priority to U.S. patent application Ser. No. 60/068,754, filed Dec. 23, 1997.

STATEMENT OF RIGHTS TO INVENTIONS MADE UNDER FEDERALLY SPONSORED RESEARCH

Not applicable.

TECHNICAL FIELD

This invention relates to derivatized carbohydrates, compositions comprised thereof and methods for their use. The derivatized carbohydrates can be used to form solid delivery systems useful for the dissolution, encapsulation, storage and delivery of a variety of therapeutic and diagnostic molecules.

BACKGROUND ART

Solid delivery systems are useful in a wide variety of applications such as controlled release of labile molecules, particularly bioactive materials such as organic pharmaceutical compounds, enzymes., vaccines and biological control agents such as pesticides and pheromones.

Drugs and other biologically active agents are frequently administered orally by means of solid dosage forms, such as tablets and capsules. Other oral solid dosage forms include lozenges and other hard candies. Solid dosage forms can also be implanted, such as subcutaneously for drug delivery. Additionally, solid dosage forms can be delivered intravenously, or by inhalation to the pulmonary system.

Solid dose delivery of bioactive materials to biological tissues such as mucosal, dermal, ocular, subcutaneous, intramuscular, intradermal and pulmonary offers several advantages over methods such as hypodermic injection and transdermal administration via so-called "patches". Using injection, there is a risk of infection using conventional needles and syringes. Dosing using multidose vials is sometimes variable, and physical discomfort often attends hypodermic injection. Devices used for administering drugs transdermally usually comprise a reservoir layer of drug and a laminated composite which adheres to the skin, i.e., transdermal patches, such as described in U.S. Pat. No. 4,906,463. Many drugs can not be effectively delivered transdermally, nor have transdermal drug release rates for those capable of such delivery been perfected. Additionally, transdermal patches often cause topical reactions, in many instances precluding their long-term use.

Subdermal implantable therapeutic systems have been formulated for slow release of certain pharmaceutical agents for extended periods of time such as months or years. A well-known example is the Norplant® implant for delivery of steroid hormones. In membrane permeation-type controlled drug delivery, the drug is encapsulated within a compartment enclosed by a rate-limiting polymeric membrane. The drug reservoir can contain either drug particles or a dispersion (or solution) of solid drug in a liquid or a solid type dispersing medium. The polymeric membrane can be fabricated from a homogeneous or a heterogeneous nonporous polymeric material or a microporous or semipermeable membrane. The encapsulation of the drug reservoir inside the polymeric membrane can be accomplished by molding, encapsulation, microencapsulation, or other techniques.

The implants release drugs by dissolution of the drug in the inner core and slow release across the outer matrix. The drug release from this type of implantable therapeutic system is dependent on drug dissolution rate in the polymeric membrane, often causing a biphasic release rate. The inner core substantially dissolves; however, generally, the outer matrix does not dissolve.

Implants are placed subcutaneously by making an incision in the skin and forcing the implants between the skin and the muscle. At the end of their use, if not dissolved, these implants must be surgically removed. U.S. Pat. No. 4,244,949 describes an implant which has an outer matrix of an inert plastic such as polytetrafluoroethylene resin.

Other implantable therapeutic systems involve matrix diffusion-type controlled drug delivery. The drug reservoir is formed by the homogeneous dispersion of drug particles throughout a lipophilic or hydrophilic polymer matrix. The dispersion of drug particles in the polymer matrix is accomplished by blending the drug with a viscous liquid polymer or a semisolid polymer at room temperature, followed by cross-linking of the polymer, or by mixing the drug particles with a melted polymer at an elevated temperature. The drug reservoir can also be fabricated by dissolving the drug particles and/or the polymer in an organic solvent followed by mixing and evaporation of the solvent in a mold at an elevated temperature or under vacuum. The rate of drug release from this type of delivery device is generally not constant. An example of this type of implantable therapeutic system is the Compudose implant.

A variety of formulations have been provided for administration in aerosolized form to mucosal surfaces, particularly "by-inhalation" (naso-pharyngeal and pulmonary). Compositions for by-inhalation pharmaceutical administration generally comprise a liquid formulation of the pharmaceutical agent and a device for delivering the liquid in aerosolized form. U.S. Pat. No. 5,011,678 describes suitable compositions containing a pharmaceutically active substance, a biocompatible amphiphilic steroid and a biocompatible (hydro/fluoro) carbon propellant. U.S. Pat. No. 5,006,343 describes suitable compositions containing liposomes, pharmaceutically active substances and an amount of alveolar surfactant protein effective to enhance transport of the liposomes across a pulmonary surface. U.S. Pat. No. 5,608,647 describes methods for administering controlled amounts of aerosol medication from a valved canister.

One drawback to the use of aerosolized formulations is that maintenance of pharmaceutical agents in aqueous suspensions or solutions can lead to aggregation and loss of activity and bioavailability. The loss of activity can be partially prevented by refrigeration; however, this limits the utility of these formulations. The use of powdered formulations overcomes many of these drawbacks. The requisite particle size of such powders is 0.5–5 microns in order to attain deep alveolar deposition in pulmonary delivery. Unfortunately, powders of such particle size tend to absorb water and clump, thus diminishing deposition of the powder in the deep alveolar spaces. PCT GB95/01861 described powders suitable for use in by-inhalation delivery. The powders are of uniform particle size and can be produced with varying degrees of hydrophobicity to reduce clumping and increase drug release in the surfactant environment of the lung.

Solid dose delivery vehicles for ballistic, transdermal administration have also been developed. For example, in U.S. Pat. No. 3,948,263, a ballistic animal implant comprised of an exterior polymeric shell encasing a bioactive material is described for veterinary uses. Similarly, in U.S. Pat. No. 4,326,524, a solid dose ballistic projectile comprising bioactive material and inert binder without an exterior casing is disclosed. Delivery is by compressed gas or explosion. Ballistic delivery at the cellular level has also been successful. Klein (1987) *Nature*, 327:70–73. There are few existing formulations suitable for ballistic delivery. Powder formulations of pharmaceuticals generally used are unsuitable for ballistic administration, because they vary in size, shape and density. The particles described in PCT GB95/01861 are useful for ballistic delivery due to their discrete size.

For drug delivery, it is advantageous to provide solid drug delivery systems of defined size, shape, density and dissolution rate. It is also advantageous to provide solid drug delivery systems that are capable of sustained, controlled release of the drug. It is further advantageous to provide solid dose delivery systems that can be formulated using simple and economical methods.

PCT/GB 90/00497 describes slow release glassy systems for formation of implantable devices. The described implants are bioabsorbable and need not be surgically removed. However, these devices are severely limited in the type of bioactive material that can be incorporated as these must be stable to heat and/or solvent to enable incorporation into the delivery device. PCT WO 93/10758 describes a carbohydrate glass matrix for the sustained release of a therapeutic agent, which includes a carbohydrate, a therapeutic agent, an agent that inhibits recrystallization of the matrix, and a water insoluble wax which modifies release of the therapeutic agent from the matrix.

PCT WO 96/03978 describes solid dose delivery systems, which include a vitreous vehicle loaded with a bioactive substance, and which are capable of releasing the substance at a controlled rate. The controlled release is achieved by the use of glass-forming, hydrophobically derivatized carbohydrates as solid vehicles, with the choice of derivative group selected to reduce solubility of the matrix material in aqueous media.

All references cited herein are hereby incorporated herein by reference.

DISCLOSURE OF THE INVENTION

Derivatized carbohydrates are provided, as well as compositions comprised thereof and methods of use thereof. The derivatized carbohydrates are generally polyol carbohydrates, wherein at least a portion of the hydroxyl groups on the carbohydrate are substituted with a branched hydrophobic chain, such as a hydrocarbon chain, via, for example, an ether or ester linkage. The derivatized carbohydrates are in one embodiment oligosaccharide ester derivatives, such as ester derivatives of disaccharides.

The derivatized carbohydrates can be formed by modification of carbohydrates. Suitable carbohydrates include, but are not limited to, glucose, lactose, cellobiose, sucrose, trehalose, raffinose, melezitose and stachyose. The hydroxyl groups of the carbohydrate can be substituted, for example via ester or ether linkages, with a branched hydrocarbon chain, such as a C3 to C30 branched hydrocarbon chain. The branched hydrocarbon chain can be a C3 to C30 hydrocarbon chain, for example, a C3 to about a C20 hydrocarbon chain. In a preferred embodiment, the hydrocarbon chain includes about a C3 to C8 hydrocarbon chain. The carbohydrate can be substituted, for example, by esterification of one or more of the hydroxyl groups on the carbohydrate with an acid such as a fatty acid including a branched hydrocarbon chain. Mixed esters and ethers of acids including a branched hydrocarbon chain can be formed, e.g., isobutyrate, pivalate, 2,2-dimethylbutyrate, 3,3-dimethylbutyrate, and 2-ethyl butyrate. Optionally, one or more of the remaining hydroxyl groups can be substituted via an ester bond with an acid such as acetate, propionate, or butyrate.

In one embodiment, the substituted carbohydrate can be substituted trehalose (Formula 1) substituted sucrose (Formula 2), substituted lactose (Formula 3), or substituted cellobiose (Formula 4), as shown below. Both α and β anomers and mixtures thereof are encompassed by the invention.

Formula 1

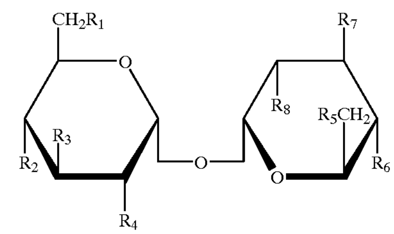

Formula 2

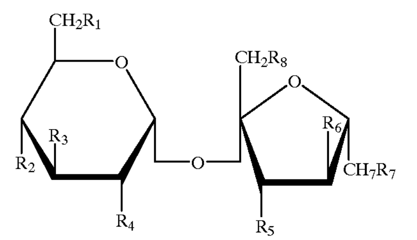

Formula 3

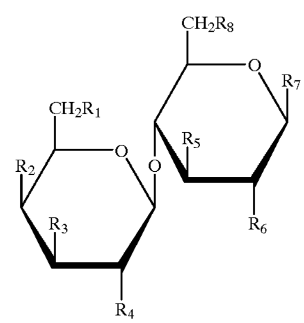

Formula 4

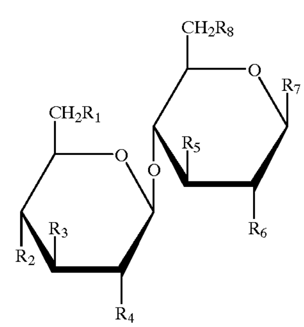

In each of Formulas 1–4, one or more of $R_{1\text{-}8}$ are independently $NHR_9$, $N(R_9)_2$, $O(C{=}O)R_9$, or $OR_9$, wherein $R_9$ is a branched, saturated or unsaturated, C3–C20 hydrocarbon, e.g., a C3–C8 hydrocarbon, and preferably a C5–C6 hydrocarbon. $O(C{=}O)R_9$ can be, for example, an acid acyl group of an acid such as isobutyrate, pivalate, 2,2-dimethylbutyrate, 3,3-dimethylbutyrate, 2-ethyl butyrate. In each of Formula 1–4, the remainder of $R_{1-8}$ are independently OH, $NHR_{10}$, $N(R_{10})_2$, $O(C=O)R_{10}$, or $OR_{10}$, wherein $R_{10}$ is alkyl, for example a C1–C4 alkyl group, such as methyl, butyl, or propyl.

Preferred derivatized carbohydrates include trehalose hexa-3,3-dimethylbutyrate, trehalose diacetate-hexa-3,3-dimethylbutyrate, trehalose octa-3,3-dimethylbutyrate, lactose isobutyrate-heptaacetate, lactose 3-acetyl-hepta-3,3-dimethylbutyrate and lactose octa-3,3-dimethylbutyrate.

Derivatized carbohydrates within the scope of the invention further include carbohydrates, such as disaccharides, wherein one or more of the free hydroxyl groups are derivatized, for example into an amine or sulfur group, to which hydrophobic branched hydrocarbon chains can be attached, for example, via an amide or thiol linkage.

Compositions, such as delivery systems, comprising the derivatized carbohydrates, and other components such as bioactive agents, carbohydrates, lipids, surfactants, binders, and any other constituents suitable for use in drug delivery are also encompassed by the invention. A wide variety of compositions can be incorporated into the compositions including diagnostic, therapeutic, prophylactic and other biologically active agents. The compositions can be in a vitreous or crystalline form, or mixtures thereof.

Solid dose delivery systems including a substituted carbohydrate can have incorporated therein a substance capable of being released from the solid delivery system. In a preferred embodiment, the solid dose delivery system comprises the substituted carbohydrate in the form of a vitreous glass matrix having the substance incorporated therein. Advantageously, drugs and bioactive agents are thereby provided in a solid, non-hygroscopic, glassy matrix, which undergoes a controlled, surface-led devitrification when immersed in aqueous environments and subsequently effects a sustained release of drugs therein.

Properties of the glassy matrix, such as the release rate of the substance, can be modulated by choice of modified carbohydrate, and other incorporated materials. The glass matrix can be modified, for example, by the addition of different glass formers with known release rates. Other materials can be incorporated into the glass matrix during processing to modify the properties of the final composition, including physiologically acceptable glass formers such as carboxylate, nitrate, sulfate, bisulfate, and combinations thereof. The delivery systems can further incorporate any other suitable carbohydrate and/or hydrophobic carbohydrate derivative, such as glucose pentaacetate or trehalose octaatacetate.

The delivery systems can be in any of a variety of forms including a lozenge, tablet, disc, film, suppository, needle, microneedle, microfiber, particle, microparticle, sphere, microsphere, powder, or an implantable device.

The invention further encompasses methods of making the delivery systems. In one embodiment, the method comprises forming or obtaining a substituted carbohydrate capable of forming a vitreous glass; processing the substituted carbohydrate and a substance to be released therefrom; and forming a solid matrix having the substance incorporated therein.

The processing step can be implemented by melting the substituted carbohydrate and incorporating the substance in the melt, at a temperature sufficient to fluidize the substituted carbohydrate, and insufficient to substantially inactivate the substance, and then quenching the melt. The melt can be processed into a variety of forms. The processing step can be also implemented by dissolving or suspending the substituted carbohydrate and the substance in a solvent effective in dissolving at least one of the derivatized carbohydrates and the substance, and evaporating the solvent.

The invention also encompasses methods of delivering bioactive materials by providing the delivery systems described above and administering the system to a biological tissue. Administration can be by any suitable means including mucosal, oral, topical, subcutaneous, intraperitoneal, intradermal, intramuscular, intravenous and by-inhalation.

The delivery systems are uniquely suited to delivery of hydrophobic substances such as pesticides, pheromones, steroid hormones, peptides, peptide mimetics, antibiotics and other organic pharmaceuticals such as synthetic corticosteroids, bronchodilators, immumodulators and immunosuppressants. The invention encompasses these delivery systems. The delivery systems are also suitable for delivery of a wide variety of non-medical substances, such as compounds used in agricultural applications, including pesticides, enzymes or other substances added to laundry detergents; and dyes or colorants.

BEST MODE FOR CARRYING OUT THE INVENTION

Figure 1:
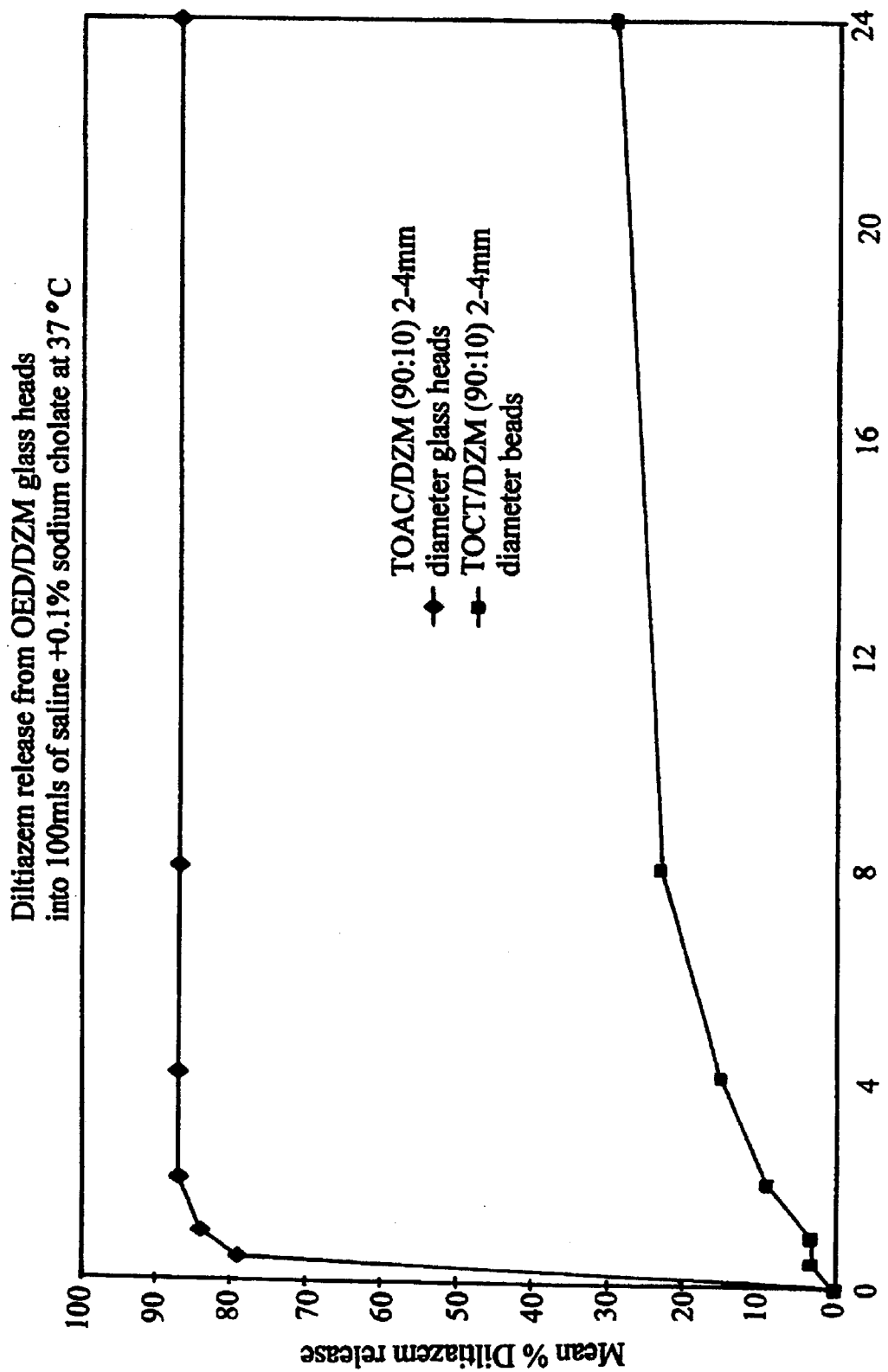
FIG. 1 is a graph depicting the release of a model hydrophilic bioactive agent, diltiazem hydrochloride (DZM) formulated (10% loading) in a single straight chain hydrophobically derivatized carbohydrate (HDC), trehalose octaacetate (closed diamonds), or branched chain HDC, trehalose octa-3,3,dimethylbutyrate (closed squares) showing the much slower release of DZM from the branched chain HDC formulation in a standard US Pharmacopeia (USP) in vitro dissolution test.

To improve the glass-forming characteristics of such hydrophobically derivatized carbohydrates, increasing the carbon chain length of the derivative group was examined, but it was found that this parameter is limited, as longer carbon straight chains than, for example C4, yield oils and not solids. It was found that, surprisingly, the use of longer carbon chains in a branched chain instead gave hydrophobically derivatized carbohydrates that formed suitable glasses, both vitreous and crystalline, for use to formulate actives, and facilitate their controlled delivery, enabling their use in solid dose delivery systems.

Derivatized carbohydrates are provided, as well as compositions comprised thereof and methods of use thereof. The derivatized carbohydrates are generally carbohydrates wherein at least a portion of the hydroxyl groups on the carbohydrate are substituted with a branched hydrophobic chain, such as a hydrocarbon chain, via, for example, an ether or ester linkage. The derivatized carbohydrates can be formed by modification of carbohydrates, including, but not limited to, glucose, lactose, cellobiose, sucrose, trehalose, raffinose, melezitose and stachyose. The hydroxyl groups of the carbohydrate can be substituted, for example via ester or ether linkages, with a branched hydrocarbon chain, for example a C3 to about a C20 hydrocarbon chain. In a preferred embodiment, the hydrocarbon chain is about a C3 to C8 hydrocarbon chain. Preferred derivatized carbohydrates include trehalose hexa-3,3-dimethylbutyrate; trehalose diacetate-hexa-3,3-dimethylbutyrate; trehalose octa-3,3-dimethylbutyrate; lactose octa-3,3-dimethylbutyrate; lactose 3-acetyl-hepta-3,3-dimethylbutyrate; and lactose isobutyrate-heptaacetate.

The derivatized carbohydrates are particularly useful in forming solid vehicles, such as vitreous glass matrices. The solid vehicles, such as vitreous glasses, can be processed into different solid forms, including tablets, powders, lozenges, implants and microspheres. A wide variety of substances can be incorporated into the solid matrices, including diagnostic, therapeutic, prophylactic, antimicrobial, insecticidal, environmental, and other bioactive agents. In the medical field, the solid matrices are useful as biodegradable solid materials for controlled delivery and release of the incorporated substance.

Formation of Derivatized Carbohydrates

The derivatized carbohydrates are formed in one embodiment by the esterification of the free hydroxyl groups on a carbohydrate. Additional other methods known in the art can be used such as etherification of the free hydroxyls. In one embodiment, at least a portion of the free hydroxyl groups are esterified with a branched hydrocarbon chain acid, or mixtures thereof. Additionally, optionally, all or a portion of the remainder of the free hydroxyls are esterified with another acid, such as alkyl acids, e.g., acetic acid, propionic acid, butyric acid, or mixtures thereof. A wide variety of partial and mixed esters can be formed. Suitable acids for ester formation with free hydroxyls on the carbohydrate that include a branched hydrocarbon chain include isobutyrate, pivalate, 2,2-dimethylbutyrate, 3,3-dimethylbutyrate, and 2-ethyl butyrate.

Carbohydrates which can be substituted at the hydroxyl group include disaccharides such as trehalose, sucrose, lactose and cellobiose, the structures of which are shown below. Either pure anomers or anomer mixtures can be used.

Formula 5

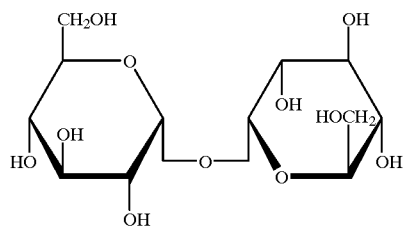

Trehalose (α-D-Glucopyranosyl-α-D-glucopyranoside)

Formula 6

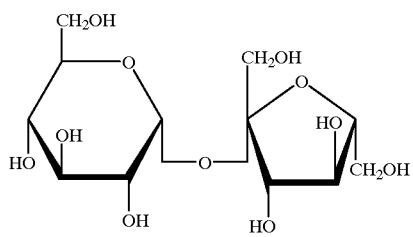

Sucrose (α-D-glucopyranosyl-β-D-Fructofuranoside)

Formula 7

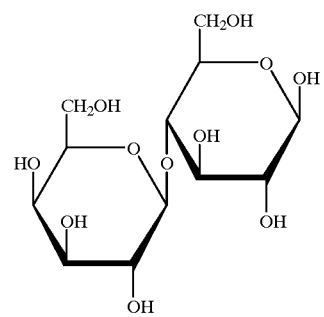

Lactose (4-O-β-D-Galactooyranosyl-D-glucose)

Formula 8

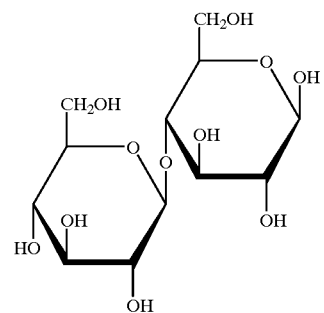

Cellobiose (4-O-β-D-Glucopyranosyl-D-glucose)

Methods for esterifying the carbohydrates are available in the art. For example, the carbohydrates can be treated with dimethylbutyroyl chloride in anhydrous pyridine to form the dimethylbutyroylated carbohydrate. Additionally, partial or mixed esters can be formed by manipulation of the reaction conditions and reagent amounts. Such partial and/or mixed esters are also encompassed by the invention.

The invention encompasses a variety of derivatized carbohydrates. Preferred derivatized carbohydrates include trehalose hexa-3,3-dimethylbutyrate, trehalose diisobutyrate-hexaacetate, trehalose diacetate-hexa-3,3-dimethylbutyrate, trehalose octa-3,3-dimethylbutyrate and lactose isobutyrate-heptaacetate.

The reaction product can be characterized structurally by methods known in the art, including, but not limited to, nuclear magnetic resonance spectroscopy (NMR) and its material science properties characterized by differential scanning calorimetry (DSC). The characteristic melting points and Tgs (glass transition temperatures) for the derivatized carbohydrates can also be determined by DSC and other methods known in the art.

Properties of Derivatized Carbohydrates

Many carbohydrates fail to readily crystallize when dried from solvent. In the absence of crystal growth, an alternative solid state, that of an amorphous, optically transparent vitreous glass is formed. A thermodynamic transition (Tg), measured by calorimetry, is characteristic of the viscous state and defines the temperature range over which the highly viscous state collapses into a more fluid rubbery state. Eventually, as the temperature continues to rise, the viscosity will fall further, resulting in a liquid melt.

In the usual process to form a vitreous glass, a high temperature melt is quenched (cooled quickly) to solidify without crystallization to a vitreous glass. Most glassy materials can theoretically quench to a vitreous glass, however, factors such as low melt viscosity, thermodynamically favorable crystalline states and thermal degradation, limit their potential to form vitreous rather than crystalline solids.

The glass matrices formed from derivatized carbohydrates as described herein can be used to stabilize labile bioactive molecules immobilized within the glassy matrix, both crystalline and vitreous. Preferably, the glassy state is vitreous. Preferred derivatized carbohydrates have high Tgs in the vitreous form, e.g., about 40° C. to 85° C., and are physically stable. The vitreous glass matrices formed therefrom have increased hydrophobicity, and thus have many applications as drug delivery vehicles, particularly for administration as sustained or delayed release forms. The derivatized carbohydrates permit solid matrices to be formed therefrom with selected controlled release properties. Without being limited to any one theory, it is believed that when the solid amorphous matrix is immersed in aqueous environments, drug release is effected by a controlled devitrification or crystallization, which begins over the surface of the glass particle. As water interacts with the glass, the devitrification front proceeds further into the glass. The crystalline matrix thus formed allows the previously entrapped drug to diffuse into the surrounding environment at a rate dependent on both HDC and drug.

The invention enables the preparation and use of derivatized carbohydrates having glass transition temperatures (Tgs) high enough to form stable glasses to allow the formulation of actives such as drugs. In parallel, the glasses undergo a slow, controlled devitrification when immersed in water. The methods of the invention permit the formulation of drugs in very hydrophobic glassy matrices, which can sustain drug release over long time periods.

Derivatized carbohydrates can also be used to form solid matrices that have a partially or substantially crystalline structure. Additionally, glasses can also be formed which form a partially or substantially crystalline structure over time after incorporation of active.

Using the methods disclosed herein, in one embodiment, $C_5$ and $C_6$ branched chain fatty acid derivatives of trehalose, and other carbohydrate molecules such as lactose, cellobiose, sucrose, raffinose and stachyose can be made, which can be melted and quenched to glasses with higher Tgs, e.g., greater than about 30° C., preferably greater than about 40° C.

The Tgs of the vitreous forms of the compositions encompassed herein are typically less than about 200° C., typically about 10° C. to 100° C., preferably about 20° C. and 85° C. The derivatized carbohydrates can be used to form vitreous glass matrices, wherein the tendency to crystallize from the melt or with reducing solvent, is low. Mixtures of derivatized carbohydrates also can be used to form the glass matrices. Glasses formed using the derivatized carbohydrates preferably have melt temperatures suitable for the incorporation of substances such as biologically active compounds, without thermal degradation, and have Tgs above ambient temperatures.

Both devitrification of the vitreous matrix and the fluidity of the melt at temperatures close to Tg can be controlled by choice of the degree and type of substitution of the carbohydrate, and by the addition of modifiers such as other derivative sugars and certain organic compounds. Suitable derivative sugars and organic compounds are described for instance, in PCT GB95/01861.

As used herein, ambient temperatures are those of the surrounding environment of any given environment. Typically, ambient temperatures are "room temperature" which is generally 20–22° C. However, ambient temperature of a "warm room" (for bacteriological growth) can be 37° C. Thus, ambient temperature is readily determined from the context in which it is used and is well understood by those of skill in the art.

Formation of Delivery Systems

The derivatized carbohydrates provided herein can be used to form a biodegradable delivery system, optionally with a substance incorporated therein, such as a therapeutic substance. The derivatized carbohydrates are referred to herein as the "vehicle" used to form the delivery system. As used herein, the term "delivery system" refers to any form of the substituted carbohydrate having a substance incorporated therein. Preferably, the delivery system is in the form of a solid matrix having the substance incorporated therein. The matrix can be designed to have a desired release rate of the substance incorporated therein, by selection of the material forming the matrix, selection of the conditions of forming the matrix, and by the addition of other substances which can modify the rate of release.

The derivatized carbohydrates readily form glasses either from a quenched melt or an evaporated organic solvent. Examples of methods of forming amorphous carbohydrate glass matrices are described in "Pharmaceutical Dosage Forms," Vol. 1 (H. Lieberman and L. Lachman, Eds.) 1982.

The derivatized carbohydrates and substance or substances to be incorporated can be intimately mixed together in the appropriate molar ratios and melted until clear. Suitable melting conditions include, but are not limited to, melting in open glass flasks at about 30–250° C. for about 1–2 minutes. This results in a fluid melt which can be allowed to cool slightly before dissolving the substance in the melt, if required, and quenching to glass for instance by pouring over a brass plate or into a metal mould for shaped delivery vehicles. The melts can also be quenched by any methods including spray chilling. Melt temperature can be carefully controlled and substances can be incorporated into the derivatized carbohydrates either in the pre-melted formulation, or stirred into the cooling melt before quenching.

The melts are thermally stable and allow the incorporation of molecules without denaturation, or suspension of core particles without alteration of their physical nature. The glass melts can be used also to coat micron-sized particles. This is particularly important in the formulation of non-hygroscopic powders containing hygroscopic actives for by-inhalation administration of therapeutic agents. Compositions made by this process are also encompassed by this invention.

Alternatively, delivery systems can be formed by evaporation of the derivatized carbohydrates and substance to be incorporated in solution in a solvent or mixture thereof. Suitable organic solvents include, but are not limited to, dichloromethane, chloroform, dimethylsulfoxide, dimethylformamide, ethyl acetate, acetone and alcohols. The type of solvent is immaterial as it is completely removed on formation of the delivery system. Preferably, both the substituted carbohydrate and substance to be incorporated are soluble in the solvent. However, the solvent can dissolve the substituted carbohydrate and allow a suspension of the substance to be incorporated in the matrix. In one embodiment, on concentrating the solvent, crystallization of the derivatized carbohydrates does not occur. Instead, a vitreous solid is produced, which has similar properties to the quenched glass. Alternatively, solid matrices which are partially, substantially or fully crystalline can be formed. Substances can be incorporated easily either in solution or as a particle suspension.

In one embodiment, a solution of the substance to be incorporated, containing a sufficient quantity of substituted carbohydrate to form a glass on drying, can be dried by any method known in the art, including, but not limited to, freeze drying, lyophilization, vacuum, spray, belt, air or fluidized-bed drying. Another suitable method of drying, exposing a syrup to a vacuum under ambient temperature, is described in PCT GB96/01367. After formation of a glass containing homogeneously distributed substance in solid solution or fine suspension in the glass, the glasses can then be milled and/or micronized to give microparticles of homogeneous defined size.

Different dosing schemes can also be achieved by the delivery system formulated. The delivery system can permit a quick release or flooding dose of the incorporated substance after administration, upon dissolving and release of the substance from the delivery system. Coformulations of vehicles with slowly water-soluble glasses and plastics such as phosphate, nitrate or carboxylate glasses and lactide/glycolide, glucuronide or polyhydroxybutyrate plastics and polyesters, provide more slowly dissolving vehicles for a slower release and prolonged dosing effect. Optionally, a substance can be incorporated into the vitreous matrix which retards recrystallization of the matrix, such as polyvinylpyrolidone, or a hydrophobic substance, to modify the release rate of the active agent, such as a water insoluble wax or a fatty acid. These are described in PCT WO 93/10758.

The delivery systems can also be coformulated with a hydrophobically-derivatized carbohydrate (HDC) glass forming material. Suitable HDC glass forming materials include, but are not limited to, those described in PCT WO 96/03978. As used herein, HDC refers to a wide variety of hydrophobically derivatized carbohydrates where at least one hydroxyl group is substituted with a hydrophobic moiety. Examples of suitable HDCs and their syntheses are described in Developments in Food Carbohydrate—2 ed. C. K. Lee, Applied Science Publishers, London (1980). Other syntheses are described for instance, in Akoh et al. (1987) *J. Food Sci.* 52:1570; Khan et al. (1993) *Tet. Letts* 34:7767; Khan (1984) *Pure & Appl. Chem.* 56:833–844; and Khan et al. (1990) *Carb. Res.* 198:275–283.

The delivery of more than one bioactive material can also be achieved using a delivery system including multiple coatings or layers loaded with different materials or mixtures thereof. Administration of the solid dose delivery systems of the present invention can be used in conjunction with other conventional therapies and coadministered with other therapeutic, prophylactic or diagnostic substances. Compositions such as these are encompassed by the invention.

The solid delivery systems can be used to deliver therapeutic agents by any means including, but not limited to, topical, transdermal, transmucosal, oral, gastrointestinal, intraperitoneal, subcutaneous, ocular, intramuscular, intravenous and by-inhalation (naso-pharyngeal and pulmonary, including transbronchial and transalveolar).

Topical administration is, for instance, by a dressing or bandage having dispersed therein a delivery system, or by direct administration of a delivery system into incisions or open wounds. Creams or ointments having dispersed therein slow release bead or microspheres of a delivery system are suitable for use as topical ointments or wound filling agents.

Compositions for transdermal administration are preferably powders of delivery systems in the form of preferably homogeneously sized microneedles or microbeads. Larger, macroscopic needle and bead forms of the delivery systems are also provided for subdermal implantation and extended drug delivery. The particle sizes should be small enough so that they cause only minimal skin damage upon administration. The powders can be prepackaged in single-dose, sealed, sterile formats. Suitable methods of transdermal administration include, but are not limited to, direct impact, ballistic, trocar and liquid jet delivery.

The delivery systems suitable for transmucosal delivery include, but are not limited to, mucoadhesive wafers, films or powders, lozenges for oral delivery, pessaries, and rings and other devices for vaginal or cervical delivery.

Compositions suitable for gastrointestinal administration include, but are not limited to, pharmaceutically acceptable powders, tablets, capsules and pills for ingestion and suppositories for rectal administration.

Compositions suitable for subcutaneous administration include, but are not limited to, various implants. Preferably the implants are macroscopic discoid, spherical or cylindrical shapes for ease of insertion and can be either fast or slow release. Since the entire implant is dissolved in the body fluids, removal of the implant is not necessary. Furthermore, the implants do not contain synthetic polymers and are biodegradable.

Compositions suitable for ocular administration include, but are not limited to, microsphere and macrosphere formulations and saline drops, creams and ointments containing these and round-ended shaped rods which fit comfortably in the lower conjunctival fornix beneath the lower eyelid.

Compositions suitable for by-inhalation administration include, but are not limited to, powder forms of the delivery systems. There are a variety of devices suitable for use in by-inhalation delivery of powders. See, e.g., Lindberg (1993) Summary of Lecture at Management Forum Dec. 6–7, 1993 "Creating the Future for Portable Inhalers." Additional devices suitable for use herein include, but are not limited to, those described in WO9413271, WO9408552, WO9309832 and U.S. Pat. No. 5,239,993.

The delivery systems are preferably biodegradable and release substances incorporated therein over a desired time period, depending on the particular application, and the composition of the system. As used herein, the term "biodegradable" refers to the ability to degrade under the appropriate conditions of use, such as outdoors, or in the body, for example by dissolution, devitrification, hydrolysis or enzymatic reaction.

Substances Incorporated in the Delivery Systems

Substances which can be incorporated into the delivery systems include, but are not limited to, medicinal or agricultural bioactive materials suitable for use in vivo and in vitro. Suitable bioactive materials include, but are not limited to, pharmaceutical agents, therapeutic and prophylactic agents, and agrochemicals such as pesticides and pheromones.

Suitable therapeutic and prophylactic agents include, but are not limited to, any therapeutically effective biological modifier. Such modifiers include, but are not limited to, pharmaceutical actives, subcellular compositions, cells, bacteria, viruses and molecules including, but not limited to, lipids, organics, proteins and peptides (synthetic and natural), peptide mimetics, hormones (peptide, steroid and corticosteroid), D and L amino acid polymers, saccharides including oligosaccharides and polysaccharides, nucleotides, oligonucleotides and nucleic acids, including DNA and RNA, protein-nucleic acid hybrids, small molecules and physiologically active analogs thereof. Further, the modifiers can be derived from natural sources or made by recombinant or synthetic means and include analogs, agonists and homologs.

As used herein "protein" refers also to peptides and polypeptides. Such proteins include, but are not limited to, enzymes, biopharmaceuticals, growth hormones, growth factors, insulin, monoclonal antibodies, interferons, interleukins and cytokines.

Organic compounds include, but are not limited to, pharmaceutically active chemicals. For instance, representative organic compounds include, but are not limited to, vitamins, neurotransmitters, antimicrobials, antihistamines, analgesics, β-agonists, β-antagonists, β-blockers, corticosteroids, and immunosuppressants.

Compositions comprising solid dose delivery systems containing prophylactic bioactive materials and carriers therefore are further encompassed by the invention. Preferable compositions include immunogens such as for use in vaccines. Preferably, the compositions contain an amount of the immunogen effective for either immunization or booster inoculation.

The invention will be further understood by the following non-limiting examples.

EXAMPLE 1

Synthesis and Physical Properties of Derivatized Carbohydrates

The carbohydrate derivatives were routinely synthesized by standard esterification of the carbohydrate with the chloride of the desired hydrocarbon side chain under anhydrous conditions and the resulting derivatives purified by standard techniques of solvent extraction and re-crystallization. For example, trehalose octa-3,3-dimethylbutyrate was synthesized by reacting 3,3,-dimethylbutyroyl chloride with trehalose in anhydrous pyridine, followed by extraction with ether, hydrochloric acid, potassium carbonate solution and water and finally re-crystallized twice from alcohol to yield colorless, needle-like crystals (~80% yield) of m.pt 138–140° C., $\alpha_D$ 112°. Trehalose hexa-3,3-dimethylbutyrate (THEX) can be prepared by protecting the 6,6'-hydroxy group of trehalose with a bulky group such as trityl or t-butyldiphenylsilyl, for example by heating trehalose and trityl chloride in pyridine. The 6,6'-ditrityltrehalose can be acylated with 3,3-dimethylbutyroyl chloride in pyridine to give 6,6'-ditritylhexa-3,3-dimethylbutyryltrehalose. The trityl group can be removed by strong acid, for example hydrogen bromide in acetic acid, to give THEX. TACT can be prepared by acylating THEX with acetic anhydride in pyridine. Suitable work-up yields the HDC in crystalline form. The physical characteristics, melting points and glass transition temperatures (Tg, ° C.) of selected carbohydrate derivatives are shown in Tables 1–5.

It was found that advantageously compounds could be made which melted, then quenched to glasses with high Tgs (>40° C.). Table 1 shows examples of fully substituted pivalate and tertbutyl acetate derivatives which show Tgs of up to 81° C., much higher than the equivalent straight chain derivatives (butyrate and valerate) which form oily syrups instead of glassy solids. This unusual property of branched-chain derivatives enables more hydrophobic derivatives (compared to the acetates) to be prepared, which permits further reduction of drug release rates for longer term applications.

Table 2 illustrates that mixed straight and branched chain ester derivatives of trehalose resulted in glasses with lower water solubilities, yet useful high Tgs. Interestingly, several of these derivatives failed to crystallize during the purification steps, thus illustrating that selected mixed ester derivatives can be difficult to crystallize. Preferred derivatives are those that form stable hydrophobic glasses with high Tgs (greater than about 40° C.), yet have a degree of instability that produces a defined, even crystal growth as the HDC glass interacts with water. The mixed ester derivatives offer a combination of both glass stability and increased hydrophobicity, which are useful to delay drug release.

Partially substituted trehalose derivatives, as shown in Tables 3, show surprising characteristics of very high Tgs, and in some cases a reluctance to also crystallize. These derivatives also fail to crystallize when immersed in water. For example, trehalose hexa-3,3-dimethylbutyrate (THEX) is stable in the glassy state when immersed in saline medium at 37° C. When the hydroxyl groups are replaced with acetates, as with trehalose diacetate hexa 3,3-dimethylbutyrate (TACT), the glass stability is reduced, though both these glasses are more stable than trehalose octa 3,3 dimethylbutyrate (TOCT). These compounds are thus useful for controlling the release rate of drugs formulated within the respective glasses. To extend this, blends of two or more HDCs permit further variations in controlling the rate of devitrification and hence drug release. For example, the pure α,β anomers of lactose isobutyrate heptaacetate crystallize from solution; however, when a small amount of the corresponding anomer is added, the blend fails to crystallize. Thus, using combinations of HDCs and/or anomers thereof, the rate of drug release can be controlled.

Table 4 illustrates some selected properties of other disaccharide ester derivatives Cellobiose octaisobutyrate has a surprisingly high melting temperature, yet is very hard to quench to glass. Lactose and cellobiose derivatives tend to have higher Tgs than trehalose and sucrose derivatives. Lactose derivatives were found to devitrify much more slowly than their corresponding trehalose derivatives despite their similar Tgs. For example, lactose isobutyrate heptaacetate is very stable in the glassy state, when immersed in water. It also has a very high Tg (Table 4).

TABLE 1

Effect of branched versus straight chains

| Derivatized Carbohydrate | M.P.(° C.) | Tg(° C.) | COMMENT |
|---|---|---|---|
| Trehalose octaacetate | 135.9 | 55 | C2 straight chain |
| Trehalose octapropionate | 47 | 3 | C3 straight chain. Glass not stable above ambient temperature |
| Trehalose octabutyrate | syrup | syrup | C4 straight chain. No glass formation |
| Trehalose octaisobutyrate | 78 | 7 | C4 branched chain. Glass formed, but not stable above ambient temperature |
| Trehalose octavalerate | syrup | syrup | C5 straight chain. No glass formation |

TABLE 1-continued

Effect of branched versus straight chains

| Derivatized Carbohydrate | M.P.(° C.) | Tg(° C.) | COMMENT |
|---|---|---|---|
| Trehalose octapivalate | 188 | 81 | C5 branched chain. Glass formed now stable above ambient temperature |

TABLE 2

Formation of mixed branched and straight chain derivatives

| Derivatized Carbohydrate | M.P.(° C.) | Tg(° C.) | COMMENT |
|---|---|---|---|
| Trehalose 6,6'-di-(2,2-dimethylbutyrate) hexaacetate | amorphous | 47 | Material not isolated in crystalline form |
| Trehalose 6,6'-di-(3,3-dimethylbutyrate) hexaacetate | 165 | 50 | |
| Trehalose 6,6'-diaacetate hexa-3,3-dimethylbutyrate | 140 | 44 | |
| Trehalose 6,6'-di-(2-ethylbutyrate) hexaacetate | 63 | 30 | |
| Trehalose 6,6'-diisobutyrate hexaacetate | 87 | 42 | |
| Trehalose 4,4'-diisobutyrate hexaacetate | 123 | 41 | |
| Trehalose 6,6'-dipropionate hexaactetate | amorphous | 43 | Material not isolated in crystalline form |
| Trehalose 4,4'-dipropionate hexaactetate | amorphous | 42 | Material not isolated in crystalline form |
| Trehalose 6,6' dipivalate hexaacetate | 159 | 56 | |

TABLE 3

Effect of partially derivatization with branched chains

| Derivatized Carbohydrate | M.P. (° C.) | Tg (° C.) | COMMENT |
|---|---|---|---|
| Trehalose octapivalate | 188 | 81 | Very hydrophobic, most resistant to devitrification in aqueous environment |
| Trehalose heptapivalate | 182 | 73 | |
| Trehalose hexapivalate | 203 | 86 | |
| Trehalose pentapivalate | amorphous | 81 | Material not isolated in crystalline form |
| Trehalose tetrapivalate | 301 | 96 | Most hydrophilic, least resistant to devitrification in aqueous environment |
| Trehalose octa-3,3-dimethylbutyrate | 139 | 42 | |
| Trehalose hexa-3,3-dimethylbutyrate | amorphous | 64 | Material not isolated in crystalline form |
| Trehalose tetra-3,3-dimethylbutyrate | 237 | 82 | |

TABLE 4

Effect of changing carbohydrate backbone

| Derivatized Carbohydrate | M.P.(° C.) | Tg(° C.) | COMMENT |
|---|---|---|---|
| α, β-Lactose octaacetate | 147 | 67 | Undefined anomeric ratio |
| α-Lactose octaacetate | 119 | 70 | |
| β-Lactose octaacetate | 87 | 63 | |
| Lactose isobutyrate heptaacetate | amorphous | 60 | 1:1 ratio of α and β anomers |
| β-Lactose isobutyrate heptaacetate | amorphous | 60 | Mixed straight and branched chain derivative |
| α-Lactose 3-acetyl-hepta-3,3-dimethylbutyrate | 128 | 48 | Mixed straight and branched chain derivative |
| α-Lactose octa-3,3-dimethyl-butyrate | 149 | 53 | C5 branched chain. Glass stable above ambient temperature |
| β-Lactose octapivalate | 168 | 88 | C5 branched chain. Glass stable well above ambient temperature |
| α-Cellobiose octaacetate | 224 | 65 | Poor glass former |
| β-Cellobiose octaacetate | 193 | 53 | Good glass former |
| β-Cellobiose methyl heptaacetate | 138 | 77 | Mixed straight chains derivative |
| β-Cellobiose ethyl heptaacetate | 182 | 52 | Longer straight chain (C2) gives lowers Tg |
| β-Cellobiose octapropionate | syrup | 15 | C3 straight chain. Glass not stable above ambient temperature |
| Raffinose undeca-isobutyrate | 83 | 15 | Branched chain derivative of trisaccharide |

EXAMPLE 2

Figure 2:
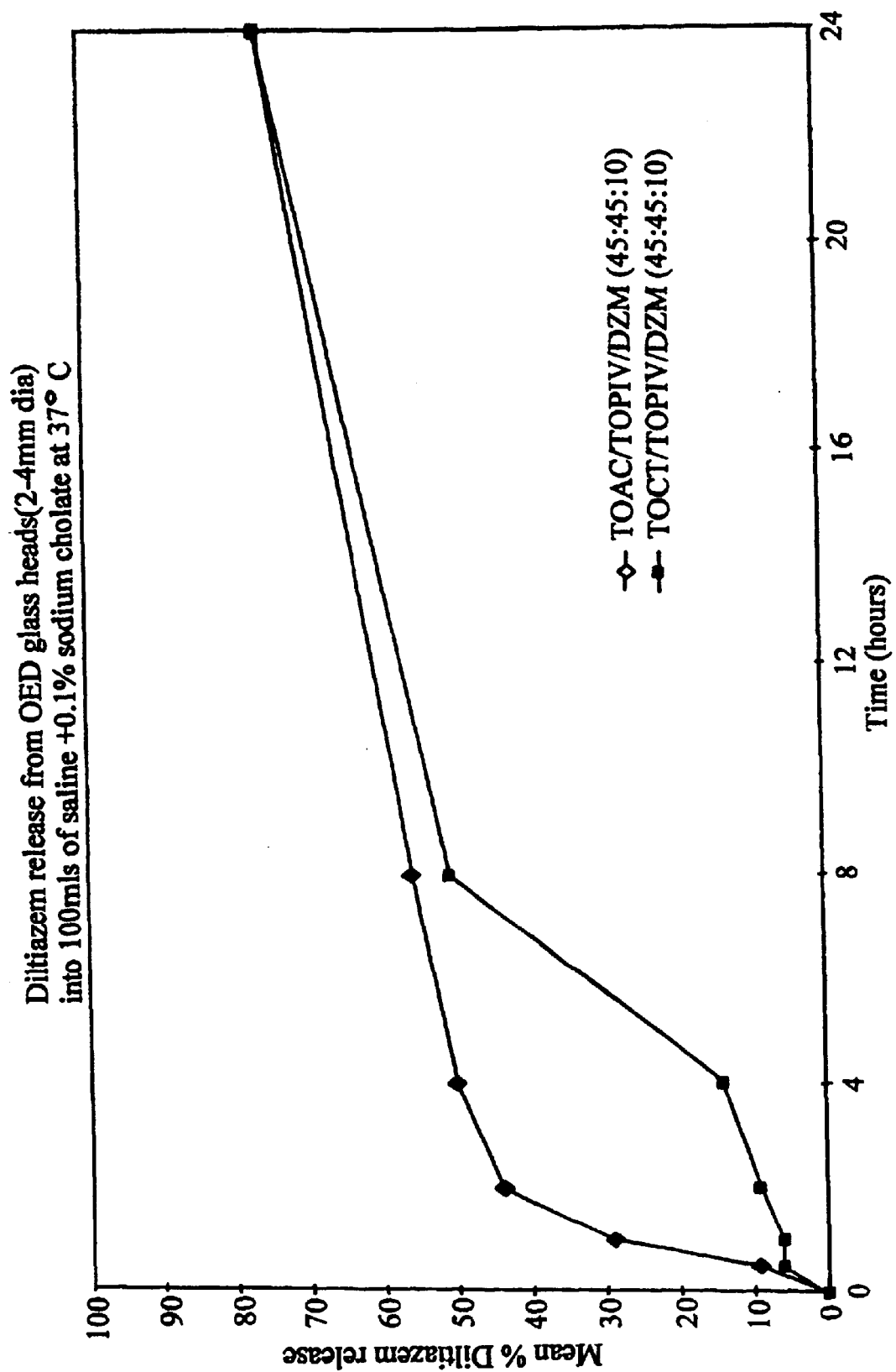
FIG. 2 is a graph depicting the release of DZM formulated (10% loading) in a mixture (1:1 ratio) of a straight (trehalose octaacetate) and branched (trehalose octapivalate) chain HDCs (closed diamonds), or two branched chain HDCs, trehalose octa-3,3,dimethylbutyrate and trehalose octapivalate (closed squares) showing the delayed release of DZM from the composite branched chain HDCs formulation in a standard USP in vitro dissolution test.

Incorporation of Active into Single and Composite Formulations of Derivatized Carbohydrates and Controlled Release In Vitro a. Formulation and Controlled Release of a Model Hydrophilic Drug The model hydrophilic drug, diltiazem hydrochloride ("hydrophilic active"), was incorporated (10% loading) into solid vehicles of the single straight chain HDC trehalose octaacetate or the branched chain HDCs trehalose octa-3,3, dimethylbutyrate and trehalose octapivalate as well as composite formulations (1:1 ratio) of the two branched-chain HDCs or the straight chain HDC trehalose octaacetate and the branched chain HDC trehalose octapivalate, by quenching from the melt. Release of the active from the HDC solid dose delivery vehicle was assessed using an in vitro USP (volume 23) type 2 dissolution test in saline containing 0.1% sodium cholate as the dissolution medium. The much slower release of HDC formulated active from a solid vehicle of the single branched chain HDC trehalose octa-3,3, dimethylbutyrate as compared to the formulation of a single straight chain HDC, trehalose octaacetate (FIG. 1) reflects the greater stability of the branched chain HDC formulation to devitrification in aqueous media. The composite formulation of the two branched chain HDCs (trehalose octa-3,3, dimethylbutyrate and trehalose octapivalate) showed a Tg of 61° C. (Table 5) and a much slower release of active as compared to the composite formulation of a mix of straight and branched chain HDCs (trehalose octaacetate and trehalose octapivalate) (FIG. 2).

The model hydrophilic drug diltiazem hydrochloride was also incorporated (5% loading) into solid vehicles of the single branched chain HDCs trehalose diisobutyrate hexaacetate and trehalose octapivalate and composite formulations (1:1 ratio) of the two branched-chain HDCs by solvent removal by rotary evaporation, in a Buchi Rotavapor R-124, of a 20% solution of active plus HDCs in a dichloromethane: acetone mixed solvent (9:1 ratio) system. The composite HDC formulation of active showed a Tg of 52.7° C. compared to Tgs of 46.5° C. (trehalose diisobutyrate hexaacetate) and 83.7° C. (trehalose octapivalate) of the single branched-chain HDC formulations of active.

b. Formulation and Controlled Release of a Model Hydrophobic Active

Figure 3:
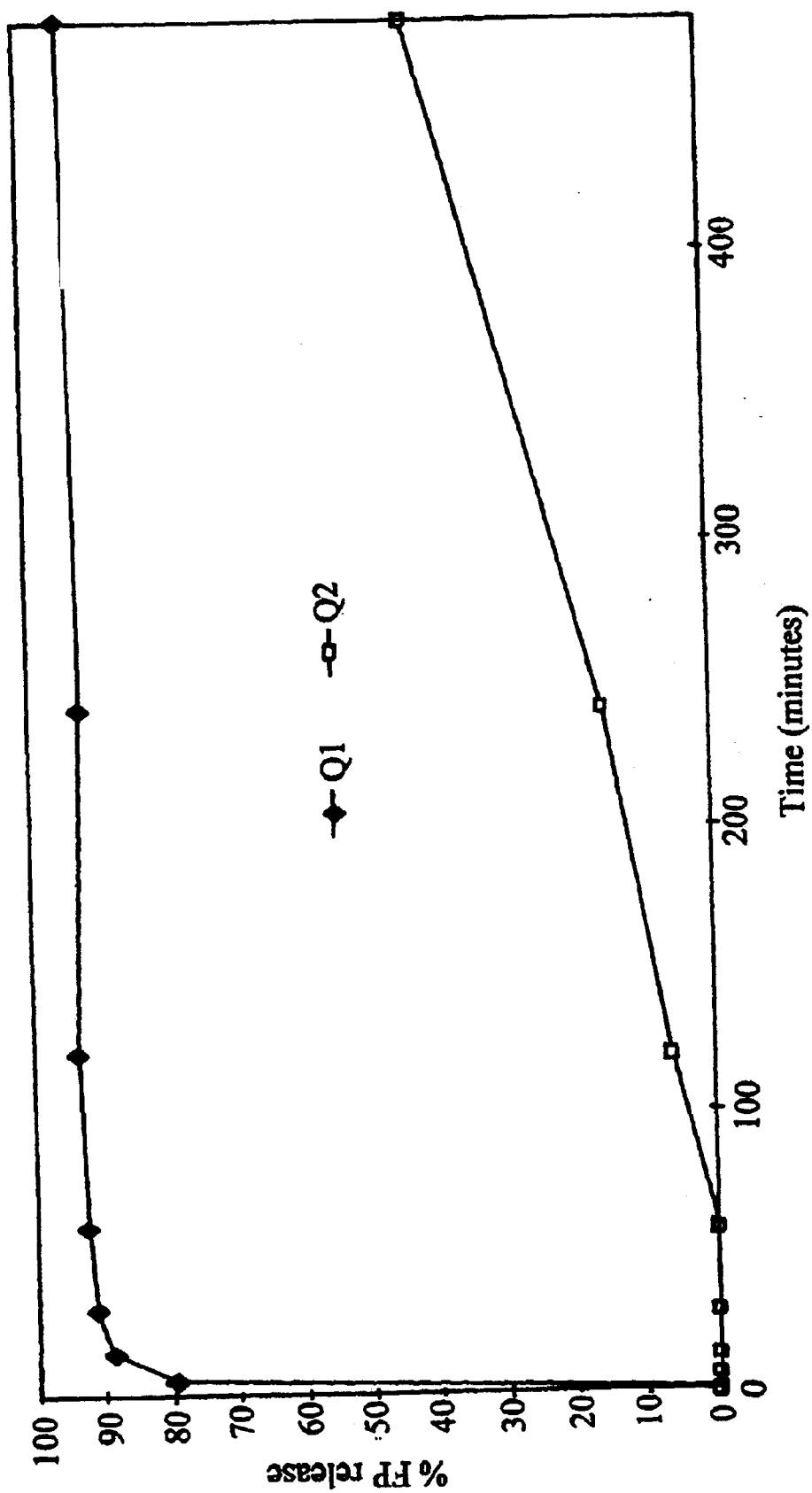
FIG. 3 is a graph depicting the release of a model hydrophobic bioactive agent, fluticasone propionate formulated in a single straight chain HDC, trehalose octaacetate (Q1, closed diamonds), or branched chain HDC, trehalose octa-3,3,dimethylbutyrate (Q2, closed squares) showing the much slower release of active from the branched chain HDC formulation in a standard USP in vitro dissolution test.

The model hydrophobic steroid fluticasone propionate ("hydrophobic active") was incorporated (5% loading) into solid vehicles of the single straight chain HDC trehalose octaacetate or the branched chain HDCs trehalose octa-3,3, dimethylbutyrate and trehalose dipropanoate hexaacetate and composite formulations (1:1 ratio) of the two branched-chain HDCs by either quenching from the melt or solvent evaporation by rotary evaporation. Melt incorporation was carried out by melting the HDCs at 150–170° C. and dissolving the active in the melt at 120–140° C. Rotary evaporation was carried out using a Buchi Rotavapor R-124 using a 20% solution of active plus HDCs in a dichloromethane: acetone mixed solvent (9:1 ratio) system. The hydrophobic active was also incorporated into solid vehicles of the branched chain HDCs, trehalose octapivalate, trehalose diisobutyrate hexaacetate and lactose isobutyrate heptaacetate, either by quenching from the melt or solvent evaporation by rotary evaporation. The Tgs for various examples of the branched chain HDC formulations containing hydrophobic active are shown in Table 5. Release of hydrophobic active from the HDC solid dose delivery vehicle was assessed using an in vitro USP (volume 23) type 2 dissolution test in saline containing 0.1% sodium cholate as the dissolution medium. The formulation of the single branched chain HDC, trehalose octapivalate (Q2), showed a much slower release of active as compared to the formulation of a single straight chain HDC, trehalose octaacetate (Q1), reflecting the greater stability of the branched chain HDC formulation to devitrification in aqueous media (FIG. 3).

c. Formulation of a Bioactive Polypeptide

As an example of a polypeptide drug, the polypeptide hormone insulin ("polypeptide active") was incorporated (10% loading) into solid vehicles of the single branched chain HDCs trehalose diisobutyrate hexaacetate and trehalose hexapivalate and composite formulations of the branched chain HDCs trehalose diisobutyrate hexaacetate and trehalose octapivalate (8:1 ratio) by solvent removal by lyophilization of a 20% solution of insulin plus HDCs in dimethylsulfoxide. The Tgs for the trehalose diisobutyrate hexaacetate, trehalose hexapivalate and composite (trehalose diisobutyrate hexaacetate: trehalose octapivalate) formulations were 50.1° C., 76.5° C. and 45° C. respectively (Table 5). Release of active from the HDC solid dose delivery vehicle was assessed using an in vitro USP (volume 23) type 2 dissolution test in saline containing 0.1% sodium cholate as the dissolution medium. The composite branched chain HDC formulation (trehalose diisobutyrate hexaacetate:trehalose octapivalate) showed a much slower release of active than the single straight chain HDC formulation (trehalose octaacetate), with 57% and 88% release of active respectively, after 1 hour in the dissolution assay.

TABLE 5

Incorporation of actives in single branched chain derivative formulations

| Derivatized Carbohydrate | Tg (° C.) | Active incorporated | Tg (° C.) | Method of incorporation |
| --- | --- | --- | --- | --- |
| Trehalose octaacetate | 50 | hydrophobic active | 53 | Melt, Solvent |
| Trehalose dipropanoate hexaacetate | 38 | hydrophobic active | 44 | Melt, Solvent |
| Trehalose octapivalate | 80 | hydrophobic active | 80 | Melt |
| Trehalose octa 3,3 dimethylbutyrate | 46 | hydrophobic active | 45 | Melt, Solvent |
| Trehalose dipropanoate hexaacetate/trehalose octa 3,3 dimethylbutyrate (1:1) | n.d. | hydrophobic active | 39 | Melt, Solvent |
| Trehalose diisobutyrate hexaacetate | 42 | hydrophobic active | 50 | Melt, Solvent |
| Lactose isobutyrate heptaacetate | 60 | hydrophobic active | 59 | Melt |
| Trehalose diisobutyrate hexaacetate | 42 | hydrophilic active | 46.5 | Melt, Solvent |
| Trehalose octapivalate | 80 | hydrophilic active | 83.7 | Melt |
| Trehalose diisobutyrate hexaacetate:trehalose octapivalate (8:1) | n.d. | hydrophilic active | 52.7 | Melt, Solvent |
| Trehalose octa 3,3-dimethylbutyrate:trehalose octapivalate (1:1) | n.d | hydrophilic active | 61 | Melt |
| Trehalose diisobutyrate hexaacetate | 42 | polypeptide active | 50.1 | Solvent |
| Trehalose hexapivalate | 86 | polypeptide active | 76.5 | Solvent |
| Trehalose octapivalate: trehalose diisobutyrate hexaacetate (8:1) | n.d | polypeptide active | 45 | Solvent |

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. A composition comprising a substituted carbohydrate and a substance capable of being released from the composition, wherein the substituted carbohydrate is trehalose diisobutyrate hexaacetate, and the substance is fluticasone.

2. The composition according to claim 1, wherein the substituted carbohydrate is in the form of a solid matrix having the substance incorporated therein.

3. The composition according to claim 1, further comprising at least one physiologically acceptable glass selected from the group consisting of carboxylate, nitrate, sulfate, bisulfate, a hydrophobic carbohydrate derivative, and combinations thereof.

4. The composition according to claim 1, wherein the composition is in the form of a solid delivery system selected from the group consisting of lozenge, tablet, disc, film, suppository, needle, microneedle, microfiber, particle, microparticle, sphere, microsphere, powder, and an implantable device.

5. The composition of claim 1, wherein the substance is fluticasone propionate.

6. The composition according to claim 1, further comprising a second substituted carbohydrate selected from the group consisting of trehalose hexa-3,3-dimethylbutyrate, trehalose diacetate-hexa-3,3-dimethylbutyrate, trehalose octa-3,3-dimethylbutyrate, lactose isobutyrate-heptaacetate, lactose 3-acetyl-hepta-3,3-dimethylbutyrate and lactose octa-3,3-dimethylbutyrate.

\* \* \* \* \*